United States Patent [19]

Berge et al.

[11] Patent Number: 4,803,293

[45] Date of Patent: Feb. 7, 1989

[54] TERTIARY AMINES

[75] Inventors: John Berge, Redhill; Richard M. Hindley, Reigate, both of England

[73] Assignee: Beecham Group plc, Middlesex, England

[21] Appl. No.: 17,002

[22] Filed: Feb. 18, 1987

Related U.S. Application Data

[63] Continuation of Ser. No. 667,757, Nov. 2, 1984, abandoned.

[30] Foreign Application Priority Data

Nov. 4, 1983 [GB] United Kingdom ................. 8329490
Dec. 22, 1983 [GB] United Kingdom ................. 8334294

[51] Int. Cl.$^4$ .......................................... C07C 101/30
[52] U.S. Cl. ..................................... 560/42; 514/866
[58] Field of Search ................... 560/42; 514/539, 866

[56] References Cited

U.S. PATENT DOCUMENTS

| | | | |
|---|---|---|---|
| 3,678,094 | 7/1972 | Shen et al. .............................. | 560/12 |
| 4,338,333 | 7/1982 | Ainsworth et al. .................... | 560/42 |

FOREIGN PATENT DOCUMENTS

| | | |
|---|---|---|
| 6735 | 1/1980 | European Pat. Off. . |
| 23385 | 2/1981 | European Pat. Off. . |
| 28105 | 5/1981 | European Pat. Off. . |
| 99107 | 2/1984 | European Pat. Off. . |

OTHER PUBLICATIONS

Kannel, *Am. Heart J.*, vol. 110, pp. 1100–1107, (1985).
Goodman et al., *The Pharmaceutical Basis of Therapeutics*, 5th Ed., MacMillan, New York, pp. 405–410, 1510–1515, 1524–1525, (1975).
Biel et al., *Progress in Drug Research*, vol. 10, pp. 46–88, Birkhauser, Stuttgart, (1966).
Kaiser, *Recent Advances in Receptor Chemistry*, pp. 189–206, (1979).

*Primary Examiner*—Michael L. Shippen
*Assistant Examiner*—Bruce D. Gray
*Attorney, Agent, or Firm*—Hopgood, Calimafde, Kalil, Blaustein & Judlowe

[57] ABSTRACT

Compounds of formula (I):

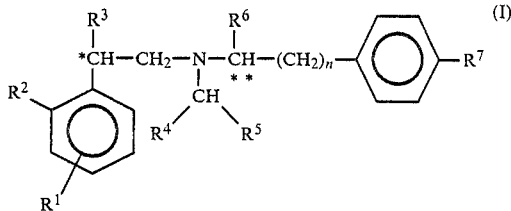

or a pharmaceutically acceptable salt thereof, in which
$R^1$ is hydrogen, halogen, or trifluoromethyl,
$R^2$ is hydrogen or halogen,
$R^3$ is hydroxyl, $C_{1-6}$ alkoxy or

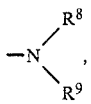

where
$R^8$ and $R^9$ are each hydrogen or $C_{1-6}$ alkyl; $R^4$ is hydrogen or $C_{1-6}$ alkyl; $R^5$ is hydrogen, $C_{1-6}$ alkyl, $C_{1-6}$ alkyl optionally substituted by hydroxy; cyano, $C_{1-6}$ alkenyl or $C_{1-6}$ alkynyl optionally substituted by carboxy or esters and amides thereof, phenyl, $C_{1-6}$ alkyl phenyl or a group

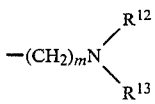

wherein $R^{12}$ and $R^{13}$ are each hydrogen or $C_{1-6}$ alkyl or together, along with the nitrogen to which they are attached, form a 5- or 6-membered ring and m is 1 or 2;
$R^6$ is hydrogen or methyl:
$R^7$ is $-O(CH_2)_aCO_2H$, $-O(CH_2)_bM$, $-CO_2H$; or amide thereof in which
a is an integer from 1 to 6,
b is an integer from 2 to 7, and
M is hydroxy, $C_{1-6}$ alkoxy or

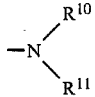

in which
$R^{10}$ and $R^{11}$ are each hydrogen or $C_{1-6}$ alkyl or

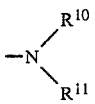

together form a five or six membered ring; and
n is 1 or 2; with the proviso that when n is 2 and $R^1$, $R^2$, $R^4$ and $R^6$ are each hydrogen and $R^3$ is hydroxyl, $R^5$ is not hydroxymethyl or 1-hydroxy ethyl when $R^7$ is $CONH_2$; processes for preparing such compounds and their use in medicine.

1 Claim, No Drawings

TERTIARY AMINES

This application is a continuation, of application Ser. No. 667,757, filed 11/2/84 abandoned.

The present invention relates to tertiary amines which have anti-hyperglycaemic and/or anti-obesity activity, to processes for their production and to their use in medicine.

European Patent Application No. 79301197.4 (Beechams) discloses compounds of formula

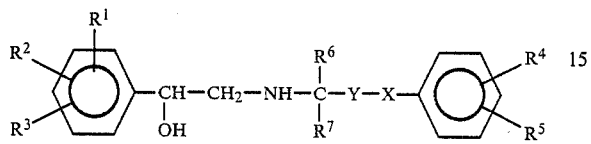

wherein
$R^1$ is hydrogen, fluorine, chlorine, hydroxyl, hydroxymethyl, methyl, methoxy, amino, formamido, acetamido, methylsulphonamido, nitro, benzyloxy, methylsulphonylmethyl, ureido, trifluoromethyl or p-methoxybenzylamino;
$R^2$ is hydrogen, fluorine, chlorine or hydroxyl;
$R^3$ is hydrogen, fluorine, chlorine or hydroxyl;
$R^4$ is a carboxylic acid group or a salt, ester or amide thereof;
$R^5$ is hydrogen, fluorine, chlorine, methyl, methoxy, hydroxyl, or a carboxylic acid group or a salt ester or amide thereof;
$R^6$ is hydrogen, methyl, ethyl or propyl;
$R^7$ is hydrogen, methyl, ethyl or propyl;
X is oxygen or a bond;
and Y is $C_{1-6}$ alkylene or a bond, which possess anti-obesity and/or hypoglycaemic activity.

It has now been discovered that a class of novel phenylethanamine derivatives have anti-hyperglycaemic and/or anti-obesity activity.

According to the present invention there is provided a compound of formula (I):

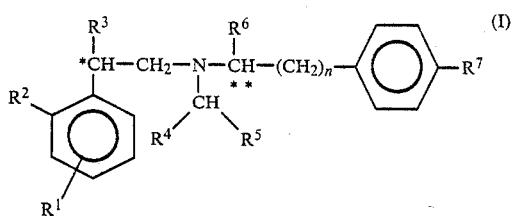

or a pharmaceutically acceptable salt thereof, in which
$R^1$ is hydrogen, halogen, or trifluoromethyl;
$R^2$ is hydrogen or halogen;
$R^3$ is hydroxyl, $C_{1-6}$ alkoxy or

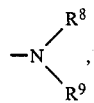

where
$R^8$ and $R^9$ are each hydrogen or $C_{1-6}$ alkyl; $R^4$ is hydrogen or $C_{1-6}$ alkyl; $R^5$ is hydrogen, $C_{1-6}$ alkyl, $C_{1-6}$ alkyl optionally substituted by hydroxy; cyano, $C_{1-6}$ alkenyl or $C_{1-6}$ alkynyl optionally substituted by carboxy or esters and amides thereof, phenyl, $C_{1-6}$ alkyl phenyl or a group

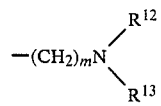

wherein $R^{12}$ and $R^{13}$ are each hydrogen or $C_{1-6}$ alkyl or together, along with the nitrogen to which they are attached, form a 5- or 6-membered ring and m is 1 or 2;
$R^6$ is hydrogen or methyl:
$R^7$ is $-O(CH_2)_aCO_2H$, $-O(CH_2)_bM$, $-CO_2H$; or an ester or amide thereof in which
a is an integar from 1 to 6,
b is an integar from 2 to 7, and
M is hydroxy, $C_{1-6}$ alkoxy or

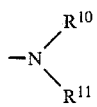

in which
$R^{10}$ and $R^{11}$ are each hydrogen or $C_{1-6}$ alkyl or

together to form a five or six membered ring; and n is 1 or 2; with the proviso that when n is 2 and $R^1$, $R^2$, $R^4$ and $R^6$ are each hydrogen and $R^3$ is hydroxyl, $R^5$ is not hydroxymethyl or 1-hydroxy ethyl when $R^7$ is $CONH_2$.

Preferably, $R^1$ is in the meta-position.
Preferably $R^5$ is hydrogen, methyl, cyano, hydroxymethyl, vinyl or ethynyl optionally substituted by carboxy or esters and amides thereof, phenyl, benzyl or piperidinomethyl.
Preferably, $R^4-CH-R^5$ represents methyl, ethyl or 2-hydroxyethyl.
Particularly preferred compounds are those wherein $R^6$ is methyl.
Preferably n is 1 and m is 1.
Pharmaceutically acceptable salts of compounds of formula (I) include acid addition salts formed with a pharmaceutically acceptable acid such as hydrochloric acid, hydrobromic acid, orthophosphoric acid, sulphuric acid, methane sulphonic acid, toluenesulphonic acid, acetic acid, propionic acid, lactic acid, citric acid, fumaric acid, malic acid, succinic acid, salicylic acid or acetylsalicylic acid.
Preferred esters of the compounds of formula (I) are those wherein $R^7$ is a $C_{1-6}$ alkyl ester of $-CO_2H$ or $-O(CH_2)_aCO_2H$. Particularly preferred esters are methyl and ethyl esters.
Preferred amides of the compounds of formula (I) are those wherein $R^7$ is converted to a group of the formula $-CONR^{10}R^{11}$ or $-O(CH_2)_aCONR^{10}R^{11}$, where $R^{10}$ and $R^{11}$ are as defined in formula (I).
When $R^6$ is methyl, the compounds of formula (I) have two asymmetric carbon atoms, marked with single and double asterisks in the formula. These compounds may, therefore, exist in four steroisomeric forms. The present invention encompasses all stereoisomers of the compounds of formula (I) whether free from other stereoisomers or admixed with other stereoisomers in any proportion and thus includes, for instance, racemic mixtures of enantiomers.

Preferably, the carbon atom marked with a single asterisk has the R configuration.

Preferably, both asymmetric carbon atoms have the R configuration.

The absolute configuration of any compound of formula (I) may be determined by conventional X-ray crystallographic techniques.

The present invention also provides a process for producing a compound of formula (I) or a salt thereof, which comprises alkylating a compound of formula (II).

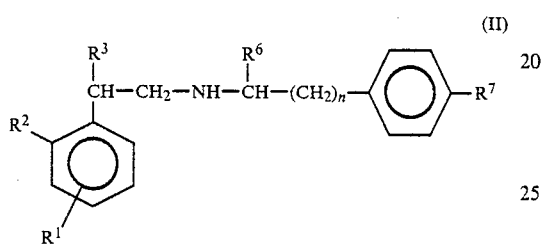

(II)

in which $R^1$, $R^2$, $R^3$, $R^6$, $R^7$, and n are as defined in formula (I).

Alkylation may be carried out by treating a compound of formula (II) with
(a) a mixture of formaldehyde and formic acid or with
(b) an aldehyde of formula $R^4$—CHO, where $R^4$ is defined in formula (I), in the presence of (i) platinum oxide, methanol and hydrogen, or (ii) sodium cyanoborohydride, or with
(c) a ketone of formula

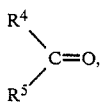

where $R^4$ and $R^5$ are as defined in formula (I), in the presence of sodium cyanoborohydride in methanol, or with
(d) an alkyl halide of formula

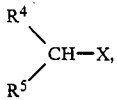

where $R^4$ and $R^5$ are as defined in formula (I) and X is halogen.

The present invention also provides a further process for producing a compound of formula (I), which comprises reacting a secondary amine of formula (III):

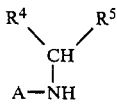

(III)

in which A represents a group of formula (IIIA) or (IIIB):

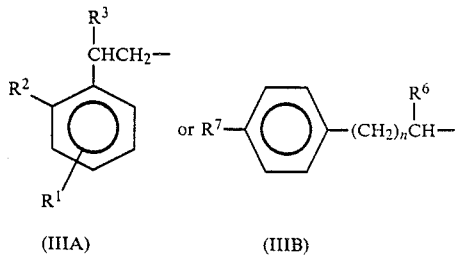

(IIIA)   (IIIB)

with a compound of formula (IV):

B-Z                                      (IV)

in which B represents a group of formula (IVA) or (IVB):

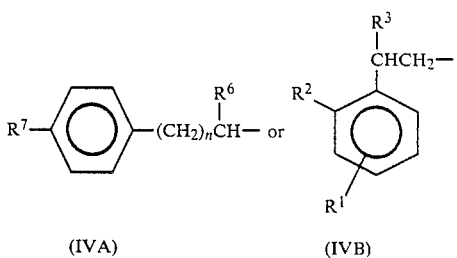

(IVA)   (IVB)

in which $R^1$, $R^2$, $R^3$, $R^4$, $R^5$, $R^6$, $R^7$, and n are as defined in relation to formula (I), and Z represents a leaving group, preferably halogen or a tosyloxy group, with the provisos that when A is a group of formula (IIIA), B is a group of formula (IVA), and when A is a group of formula (IIIB), B is a group of formula (IVB), and optionally thereafter forming a salt of the compound of formula (I) so formed and/or converting the compound of formula (I) so formed into a further compound of formula (I).

The reaction of a compound of formula (III) with a compound of formula (IV) is conveniently carried out in a solvent, preferably dimethyl sulphoxide, at elevated temperature, preferably 50° C., for about two or three days.

An alternative process for the preparation of a compound of formula (I) in which $R_3$ represents hydroxyl, comprises reacting a compound of formula (V):

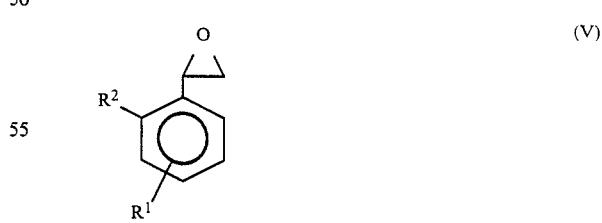

(V)

with a compound of formula (VI)

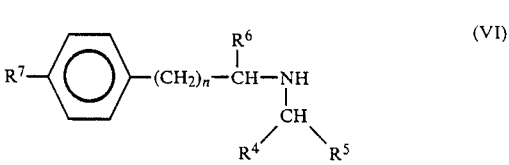

(VI)

in which $R^1$, $R^2$, $R^4$, $R^5$, $R^6$, $R^7$, and n are as defined in formula (I).

A further alternative process for preparing a compound of formula (I) in which $R^3$ represents hydroxyl, comprises reducing a compound of formula (VII)

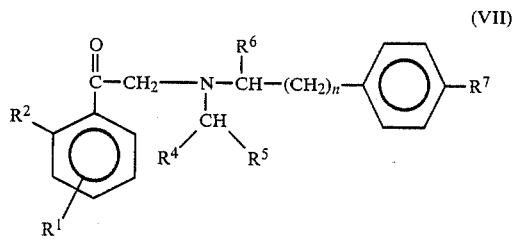

(VII)

in which $R^1$, $R^2$, $R^4$, $R^5$, $R^6$, $R^7$, and n are as defined in formula (I). Reduction may be effected by conventional chemical methods such as with lithium aluminium hydride, or sodium borohydride.

The compounds of formula (VII) may themselves be prepared by reacting an amine of formula (III) in which A represents

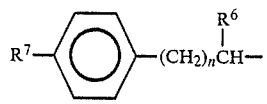

with a compound of formula (VIII)

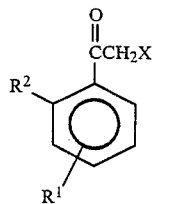

(VIII)

in which $R^1$, $R^2$, $R^6$, $R^7$, and n are as defined in formula (I), and X is halogen, preferably bromine.

Compounds of formulae (II), (III), (IV), (V), (VI) and (VIII) are either known compounds or can be prepared from known compounds by processes analogous to known processes.

The salts of compounds of formula (I) may be produced by treating the compound of formula (I) with the appropriate acid.

Compounds of formula (I) and salts thereof, produced by the above processes, may be recovered by conventional methods.

Compounds of formula (I) may be separated into diastereoisomeric pairs of enantiomers by, for example, fractional crystallisation from a suitable solvent such as methanol or ethyl acetate or a mixture thereof. The pair of enantiomers thus obtained may be separated into individual stereoisomers by conventional means such as by the use of an optically active acid as a resolving agent.

Suitable optically active acids which may be used as resolving agents are described in 'Topics in Stereochemistry', Vol. 6, Wiley Interscience, 1971, Allinger, N. L. and Eliel, W. L. Eds.

Alternatively any enantiomer of a compound of formula (I) may be obtained by sterospecific synthesis using an optically pure starting material of known configuration.

A compound of formula (I) or a pharmaceutically acceptable salt thereof (hereinafter 'the drug') may be administered as the pure drug, however, it is preferred that the drug be administered as a pharmaceutical composition also comprising a pharmaceutically acceptable carrier.

Accordingly, the present invention also provides a pharmaceutical composition comprising a compound of formula (I) or a pharmaceutically acceptable salt thereof with a pharmaceutically acceptable carrier therefor.

As used herein the terms 'pharmaceutical composition' and 'pharmaceutically acceptable' embrace compositions and ingredients for both human and veterinary use.

Usually the compositions of the present invention will be adapted for oral administration although compositions for administration by other routes, such as by injection are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or the like.

Typical carriers may, therefore, comprise such agents as microcrystalline cellulose, starch, sodium starch glycollate, polyvinylpyrrolidone, poylvinylpolypyrrolidone, magnesium stearate, sodium lauryl sulphate, sucrose and the like.

Most suitably the composition will be provided in unit dose form. Such unit doses will normally comprise 0.1 to 1000 mg of the drug, more usually 0.1 to 500 mg and favourably 0.1 to 250 mg.

The present invention further provides a method for treating hyperglycaemia in humans or non-human animals which method comprises administering an effective, non-toxic amount of a compound of formula (I) or a pharmaceutically acceptable salt thereof to hyperglycaemic humans or non-human animals.

The present invention further provides a method for treating obesity in human or non-human animals, which method comprises administering an effective, non-toxic amount of a compound of formula (I) or a pharmaceutically acceptable salt thereof to obese humans or non-human animals. Conveniently, the drug may be administered as a pharmaceutical composition as hereinbefore defined, and this forms a particular aspect of the present invention.

In treating hyperglycaemic or obese humans the drug may be taken in doses, such as those described above, one to six times a day in a manner such that the total daily dose for a 70 kg adult will generally be about 0.1 to 6000 mg, and more usually about 1 to 1500 mg.

In treating hyperglycaemic or obese animals, especially dogs, the drug may be administered by mouth, usually once or twice a day and at about 0.025 mg/kg to 25 mg/kg, for example 0.1 mg/kg to 20 mg/kg.

Within the above indicated dosage ranges, no adverse toxicological effects have been observed with the compounds of the invention.

The invention will now be illustrated with reference to the following Examples.

In the Examples, the substituents in formula (I) are as shown in the following table:

| | R¹ | R² | R³ | R⁴ | R⁵ | R⁶ | R⁷ | n |
|---|---|---|---|---|---|---|---|---|
| 1 | H | H | OH | H | H | CH₃ | CO₂CH₃ | 1 |
| 2 | H | H | OH | H | H | CH₃ | CO₂CH₃ | 1 |
| 3 | m-Cl | H | OH | H | H | CH₃ | OCH₂CO₂CH₃ | 1 |
| 4 | m-Cl | H | OCH₃ | H | H | CH₃ | OCH₂CO₂CH₃ | 1 |
| 5 | m-Cl | H | N(CH₃)₂ | H | H | CH₃ | OCH₂CO₂CH₃ | 1 |
| 6 | H | H | OH | H | CH₃ | CH₃ | CO₂CH₃ | 1 |
| 7 | H | H | OH | H | H | CH₃ | OCH₂CONHCH₃ | 1 |
| 8 | m-Cl | H | OH | H | CH₂OH | CH₃ | OCH₂CO₂CH₃ | 1 |
| 9 | m-Cl | H | OH | H | CH₃ | CH₃ | OCH₂CO₂CH₃ | 1 |
| 10 | m-CF₃ | H | OH | H | H | CH₃ | OCH₂CO₂CH₃ | 1 |
| 11 | H | H | OH | H | —C≡CH | CH₃ | CO₂CH₃ | 1 |
| 12 | 3-Cl | H | OH | H | CH=CHCO₂CH₃ | CH₃ | OCH₂CO₂CH₃ | 1 |
| 13 | 3-Cl | H | OH | H | CH₂C₆H₅ | CH₃ | OCH₂CO₂CH₃ | 1 |
| 14 | 3-Cl | H | OH | H | —C=CH₂ | CH₃ | OCH₂CO₂CH₃ | 1 |
| 15 | 3-Cl | H | OH | H | —CN | CH₃ | OCH₂CO₂CH₃ | 1 |
| 16 | 3-Cl | H | OH | H | CH₂N⟨piperidine⟩ | CH₃ | OCH₂CO₂CH₃ | 1 |
| 17 | 3-Cl | H | OH | H | H | CH₃ | OCH₂CONH₂ | 1 |
| 18 | 3-Cl | H | OH | H | Ph | CH₃ | OCH₂CO₂CH₃ | 1 |

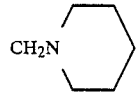

EXAMPLE 1

(RS,SR)-N-[2-(4-Carbomethoxyphenyl)-1-methylethyl]-N-methyl-2-hydroxy-2-phenylethanamine hydrochloride To a mixture of formaldehyde (0.87 ml of 37% aqueous solution) and formic acid (1.3 ml of 88% aqueous solution) was added (RS,SR)-N-[2-(4-carbomethoxyphenyl)-1-methylethyl]-2-hydroxy-2-phenylethanamine (3.13 g) and the mixture was heated on a steam-bath for 2 hours. After cooling to room temperature a saturated solution of sodium carbonate (50 ml) was added, the solution was extracted with dichloromethane, dried (magnesium sulphate), filtered and evaporated. The residue was chromatographed on silica-gel in 5% methanol-dichloromethane to give an oil which on treatment with ethereal hydrogen chloride gave the title compound, m.p. 146°–8° C. (methanol-ethyl acetate-ether).

¹H nmr δ(DMSO-d₆)

1.15 (3H, d); 2.6–3.9 (11H, complex); 5.2 (1H, t); 6.25 (1H, broad s, exchanges with D₂O); 7.25–8.10 (9H, complex); 9.95–11.0 (1H, broad d, exchanges with D₂O)

EXAMPLE 2

(RR,SS)-N-[2-(4-carbomethoxyphenyl)-1-methylethyl]-N-methyl-2-hydroxy-2-phenylethananime hydrochloride The title compound, m.p. 199°–200° C. (methanol-ethyl acetate), was obtained from (RR,SS)-N-[2-(4-carbomethoxyphenyl)-1-methylethyl]-2-hydroxy-2-phenylethanamine hemifumarate by an analogous procedure to that described in Example 1.

¹H nmr δ(DMSO-d₆)

1.15 (3H, d), 2.6–3.9 (11H, complex), 5.2 (1H, t), 6.25 (1H, broad s, exchanges with D₂O), 7.25–8.10 (9H, complex), 9.95–11.0 (1H, broad s, exchanges with D₂O).

EXAMPLE 3

(RR,SS)-N-[2-(4-carbomethoxymethoxyphenyl)-1-methylethyl]-N-methyl-2-hydroxy-2-(3-chlorophenyl)ethanamine hydrochloride The title compound, mp 127°–9° C. (methanol-diethylether) was obtained from (RR,SS)-N-[2-(4-carbomethoxymethoxyphenyl)-1-methylethyl]-2-hydroxy-2-(3-chlorophenyl)ethanamine by an analogous procedure to that described in Example 1.

¹H nmr δ(DMSO-d₆)

1.15 (3H, d); 2.60–3.90 (11H, complex); 4.75 (2H, s); 5.20 (1H, t); 6.55 (1H, broad s, exchanges with D₂O); 6.75–7.7 (8H, complex); 10.1–10.9 (1H, broad d, exchanges with D₂O).

EXAMPLE 4

(RR,SS)-N-[2-(4-carbomethoxymethoxyphenyl)-1-methylethyl]-N-methyl-2-methoxy-2-(3-chlorophenyl)ethanamine hydrochloride The title compound, mp 86°–94° C. (ethylacetate-diethyl ether) was obtained from (RR,SS)-N-[2-(4-carbomethoxymethoxyphenyl)-1-methylethyl]-2-methoxy-2-(3-chlorophenyl)ethanamine by an analogous procedure to that described in Example 1.

¹H nmr δ(DMSO-d₆)

1.15 (3H, dd); 2.60–3.85 (14H, complex); 4.65–5.3 (3H, complex); 6.85 (2H, d); 7.20 (2H, d); 7.35–7.65 (4H, complex); 10.5–11.4 (1H, broad d, exchanges with D₂O).

EXAMPLE 5

N-[2-(4-carbomethoxymethoxyphenyl)-1-methylethyl]-N-methyl-2-dimethylamino-2-(3-chlorophenyl)ethanamine dihydrochloride monohydrate The title compound, mp 128°–133° C., was prepared as a 52:48 mixture of diastereoisomers from N-[2-(4-carbomethoxymethoxyphenyl)-1-methylethyl]-2-dimethylamino-2-(3-chlorophenyl)ethanamine by an analogous procedure to that described in Example 1.

¹H nmr δ(DMSO-d₆+D₂O)

1.15 (3H, complex); 2.70 (6H, s); 2.80 (3H, s); 3.10–4.20 (8H, complex); 4.75 (2H, s); 5.20 (1H, t); 6.75–8.00 (8H, complex).

EXAMPLE 6

(RS,SR)-N-[2-(4-carbomethoxyphenyl)-1-methylethyl]-N-ethyl-2-hydroxy-2-phenylethanamine hydrochloride A mixture of acetaldehyde (2 ml) and (RS,SR)-N-[2-(4-carbomethoxyphenyl)-1-methylethyl]-2-hydroxy-2-phenyl-ethanamine (5.94 g) in methanol (100 ml) was reduced under hydrogen in the presence of 10% palladium on carbon. When hydrogen uptake ceased the catalyst was filtered off and the solvent was removed under reduced pressure. The residue was chromatographed on silica-gel in 5% methanoldichloromethane to give an oil which on treatment with an ethereal solution of hydrogen chloride gave the title compound, mp 129°–32° C. (methanol-diethyl ether).

$^1$H nmr $\delta$(DMSO-$d_6$)

1.10–1.65 (6H, complex); 2.65–4.15 (10H, complex); 5.30 (1H, complex); 6.35 (1H, broad s, exchanges with $D_2O$); 7.25–7.7 (7H, complex); 7.95 (2H, d); 10.3–10.8 (1H, broad d, exchanges with $D_2O$).

EXAMPLE 7

N-[2-(4-methylaminocarbonylmethoxyphenyl)-1-methylethyl]-N-methyl-2-hydroxy-2-phenylethanamine hydrochloride A solution of N-methyl-N-(2-[4-methylaminocarbonylmethoxyphenyl]-1-methylethyl)-α-aminoacetophenone (3.00 g) in ethanol (80 ml) was cooled to 5° C. and sodium borohydride (2.2 g) was added portionwise with stirring. On completion of the addition the mixture was stirred at 5° C. for 1 hour, quenched with saturated sodium carbonate solution, the ethanol evaporated, the residue extracted into dichloromethane and the extracts dried (magnesium sulphate), filtered and evaporated. The residue was chromatographed on silica-gel in 2% methanol-dichloromethane to give an oil which on treatment with ethereal hydrogen chloride gave the title compound, m.p. 48°–51° C.

$^1$H nmr $\delta$(DMSO-$d_6$+$D_2O$)

1.10 (3H, d); 2.65 (3H, d); 2.90 (3H, broad s); 2.4–3.9 (8H, complex); 5.15 (1H, t); 6.95 (2H, d); 7.15–7.70 (6H, complex)

EXAMPLE 8

(RR,SS)-N-[2-(4-Carbomethoxymethoxyphenyl)-1-methylethyl]-N-(2-hydroxyethyl)-2-hydroxy-2-(3-chlorophenyl)ethanamine hydrochloride To a solution of (RR,SS)-N-[2-(4-carbomethoxymethoxyphenyl)-1-methylethyl]-2-hydroxy-2-(3-chlorophenyl)ethanamine hydrobromide (4.14 g) in methyl ethyl ketone (80 ml) containing potassium carbonate (10 g) was added 2-bromoethanol (10 ml). The mixture was boiled under reflux with vigorous stirring for 18 hours, cooled, filtered and the solvent was removed under reduced pressure. The residue was chromatographed on silica gel in 5% methanoldichloromethane to give an oil which on treatment with ethereal hydrogen chloride gave the title compound m.p.91°–94° C. (methanol-diethyl ether).

$^1$H nmr $\delta$(DMSO-$d_6$)

1.15 (3H, complex); 2.5–4.15 (9H, complex); 3.75 (3H, s); 4.80 (2H, s); 5.05–5.7 (2H, complex collapsing to 1H, t on $D_2O$ exchange); 6.45 (1H, broad s, exchanges with $D_2O$); 6.9 (2H, d); 7.15–7.7 (6H, complex); 9.4–9.85 (1H, broad, s, exchanges with $D_2O$).

EXAMPLE 9

(RR,SS)-N-[2-(4-Carbomethoxymethoxphenyl)-1-methylethyl]-N-ethyl-2-hydroxy-2-(3-chlorophenyl)ethanamine hydrochloride The title compound, m.p. 128°–131° C. (dichloromethanediethyl ethyl) was obtained from (RR,SS)-N-[2-(4-carbomethoxymethoxyphenyl)-1-methylethyl]-2-hydroxy-2-(3-chlorophenyl)ethanamine and ethyl iodide by an analogous procedure to that described in Example 8.

$^1$H nmr $\delta$(DMSO-$d_6$)

1.15 (3H, complex); 1.35 (3H, t); 2.5–3.8 (7H, complex); 3.65 (3H, s); 4.75 (2H, s); 5.15 (1H, t); 6.55 (1H, d, exchanges with $D_2O$); 6.90 (2H, d); 7.10–7.60 (6H, complex); 9.6–10.2 (1H, broad s, exchanges with $D_2O$).

EXAMPLE 10

N-[2-(4-Carbomethoxymethoxyphenyl)-1-methylethyl]-N-methyl-2-hydroxy-2-(3-trifluoromethylphenyl)ethanamine hydrochloride The title compound, m.p. 95°–98° C. (dichloromethanediethyl ether) was obtained from N-[2-(4-carbomethoxymethoxyphenyl)-1-methylethyl]-2-hydroxy-2-(3-trifluoromethylphenyl)ethanamine by an analogous procedure to that described in Example 1.

$^1$H nmr $\delta$(DMSO-$d_6$)

1.15 (3H, d); 2.55–3.85 (8H, complex); 3.70 (3H, s); 4.75 (2H, s); 5.25 (1H, broad s); 6.6 (1H, broad s, exchanges with $D_2O$); 6.85 (2H, d); 7.15 (2H, d); 7.55–8.00 (4H, complex); 9.75–10.3 (1H, broad s, exchanges with $D_2O$).

EXAMPLE 11

(RR,SS)-N-[2-(4-Carbomethoxyphenyl)-1-methylethyl]-N-[prop-2-ynyl]-2-hydroxy-2-phenylethanamine hydrochloride hydrate 1-Chloro-prop-2-yne (10 ml) was added to a solution of (RR,SS)-N-[2-(4-carbomethoxyphenyl)-1-methylethyl]-2-hydroxy-2-phenylethanamine hemifumarate (5 g) in butan-2-one (100 ml) containing potassium carbonate (10 g) and potassium iodide (0.5 g). The mixture was boiled under reflux with vigorous stirring for 24 hours, cooled, filtered and the solvent was removed under vacuum. The residue was chromatographed on silica-gel (250 g) in 2% methanoldichloromethane to give an oil which on treatment with an ethereal solution of hydrogen chloride and crystallisation from dichloromethane-diethyl ether gave the title compound, m.p. 78°–82° C.

$^1$H nmr $\delta$(DMSO $d_6$-$D_2O$)

1.20 (3H, d); 2.65–4.10 (6H, complex); 3.85 (3H, s); 4.40 (2H, s); 5.25 (1H, t); 7.2–7.65 (7H, complex); 7.9–8.0 (2H, d).

EXAMPLE 12

(RR,SS)-N-[2-(4-Carbomethoxymethoxyphenyl)-1-methylethyl]-N-(3-carbomethoxyprop-2-enyl)-2-hydroxy-2-(3-chlorophenyl)ethanamine hydrochloride The title compound, m.p. 95°–96° 1 C. (dichloromethane-diethyl ether) was obtained from (RR,SS)-N-[2-(4-carbomethoxymethoxyphenyl)-1-methylethyl]-2-hydroxy-2-(3-chlorophenyl)ethanamine hydrobromide by an analogous procedure to that described in Example 11.

$^1$H nmr δ(DMSO-d$_6$)

1.20 (3H, complex); 2.60-3.80 (7H, complex); 3.70 (6H, 2 superimposed s); 4.0-4.4 (2H, complex); 4.65-4.85 (3H, complex); 5.1-5.35 (1H, t); 6.2-6.35 (1H, d); 6.1-6.7 (1H, broad s, exchanges with D$_2$O); 6.8 (2H, d); 7.15 (2H, d); 7.3-7.6 (4H, complex); 10.6-11.2 (1H, broad d, exchanges with D$_2$O).

EXAMPLE 13

(RR,SS)-N-[2-(4-Carbomethoxymethoxyphenyl)-1-methylethyl]-N-(2-phenylethyl)-2-hydroxy-2-(3-chlorophenyl)ethanamine hydrochloride The title compound, m.p. 142°-145° C. (dichloromethane-diethyl ether) was obtained from (RR,SS)-N-[2-(4-carbomethoxymethoxyphenyl)-1-methylethyl]-2-hydroxy-2-(3-chlorophenyl)ethanamine hydrobromide and 2-phenylethylbromide by an analogous procedure to that described in Example 11.

$^1$H nmr δ(DMSO-d$_6$)

1.2 (3H, complex); 2.6-4.0 (9H, complex); 3.7 (3H, s); 4.75 (2H, s); 5.3 (1H, t); 6.55 (1H, broad s, exchanges with D$_2$O); 6.85 (2H, d); 7.1-7.7 (11H, complex); 10.1-10.6 (1H, broad d, exchanges with D$_2$O).

EXAMPLE 14

(RR,SS)-N-[2-(4-Carbomethoxymethoxyphenyl)-1-methylethyl]-N-(prop-2-enyl)-2-hydroxy-2-(3-chlorophenyl)ethanamine hydrochloride The title compound, m.p. 92°-4° C. (dichloromethane-diethyl ether) was obtained from (RR,SS)-N-[2-(4-carbomethoxymethoxyphenyl)-1-methylethyl]-2-hydroxy-2-(3-chlorophenyl)-ethanamine hydrobromide and 1-bromoprop-2-ene by an analogous procedure to that described in Example 11.

$^1$H nmr δ(DMSO-d$_6$)

1.15 (3H, complex); 2.45-4.3 (7H, complex); 3.70 (3H, s); 4.75 (2H, s); 5.1-6.6 (5H, complex, 1H, exchanges with D$_2$O); 6.85 (2H, d); 7.20 (2H, d); 8.4 (4H, complex); 10.2-10.8 (1H, broad d, exchanges with D$_2$O).

EXAMPLE 15

(RR,SS)-N-[2-(4-Carbomethoxymethoxyphenyl)-1-methylethyl]-N-cyanomethyl-2-hydroxy-2-(3-chlorophenyl)ethanamine hydrochloride The title compound, mp. 146°-8° C. (dichloromethane-diethyl ether) was obtained from (RR,SS)-N-[2-(4-carbomethoxymethoxyphenyl)-1-methylethyl]-2-hydroxy-2-(3-chlorophenyl)ethanamine hydrobromide by an analogous procedure to that described in Example 11.

$^1$H nmr δ(DMSO-d$_6$)

1.10 (3H, d); 2.40-3.70 (5H, complex); 3.70 (3H, s); 4.40 (2H, s); 4.75 (2H, s); 5.20 (1H, t); 6.0-6.9 (2H, broad s, exchanges with D$_2$O); 6.85 (2H, d); 7.15 (2H, d); 7.40 (4H, complex).

EXAMPLE 16

(RR,SS)-N-[2-(4-Carbomethoxymethoxyphenyl)-1-methylethyl]-N-[2-piperidinylethyl]-2-hydroxy-2-(3-chlorophenyl)ethanamine dihydrochloride monohydrate The title compound, mp. 93°-95° C., was obtained from (RR,SS)-N-[2-(4-carbomethoxymethoxyphenyl)-1-methylethyl]-2-hydroxy-2-(3-chlorophenyl)ethanamine hydrobromide in a similar manner to that described in Example 11.

$^1$H nmr δ(DMSO-d$_6$+D$_2$O)

1.15 (3H, complex); 1.5-2.1 (6H, broad s); 2.7-4.1 (13H, complex); 3.7 (3H, s); 4.75 (2H, s); 5.25 (1H, t); 6.8 (2H, d); 7.1-7.8 (6H, complex).

EXAMPLE 17

(RR,SS)-N-[2-(4-Aminocarbonylmethoxyphenyl)-1-methylethyl]-N-methyl-2-hydroxy-2-(3-chlorophenyl)ethanamine hydrochloride hydrate To a solution of (RR,SS)-N-[2-(4-carbomethoxymethoxyphenyl)-1-methylethyl]-N-methyl-2-hydroxy-2-(3-chlorophenyl)ethanamine (2.0 g) in methanol (50 ml) was added 0.880 ammonia solution (100 ml) and the mixture was boiled under reflux for 3 hours. After cooling, water (100 ml) was added and the mixture was extracted twice with dichloromethane. The combined extracts were dried (MgSO$_4$), filtered and evaporated and the residue was purified by chromatography on silica-gel in 5% methanol-dichloromethane. The hydrochloride salt was formed in diethyl-ether and crystallisation from methanol-diethyl ether gave the title compound, m.p. 95°-98° C.

$^1$H nmr δ(DMSO-d$_6$+D$_2$O)

1.20 (3H, d); 2.55-4.20 (8H, complex); 4.30 (2H, s); 5.20 (1H, t); 6.85 (2H, d); 7.15-7.60 (6H, complex).

EXAMPLE 18

N-Benzyl-N-[2-(4-carbomethoxymethoxyphenyl)-1-methylethyl]-2-hydroxy-2-(3-chlorophenyl)ethanamine hydrochloride The title compound, m.p. 146°148° C. (dichloromethanediethyl ether) was obtained from N-[2-(4-carbomethoxyphenyl)-1-methylethyl]-2-hydroxy-2-(3-chlorophenyl)ethanamine hydrobromide by an analogous procedure to that described in Example 11.

$^1$H nmr δ(DMSO-d$_6$+D$_2$O)

1.20 (3H, d); 2.60-3.80 (5H, complex); 3.70 (3H, s); 4.5 (2H, broad s); 4.75 (2H, s); 5.45 (1H, t); 6.80 (2H, d); 7.05-7.80 (11H, complex).

EXAMPLE X 1

N-methyl-2-(4-methylaminocarbonylmethoxyphenyl)-1-methylethanamine hydrochloride 1-(4-Carbomethoxymethoxyphenyl)propan-2-one (7.5 g) was added to a 33% solution of methylamine in ethanol (150 ml) and the mixture was boiled under reflux through a Soxhlet apparatus containing potassium carbonate for 14 hours. After cooling and filtering the solution was cooled to 0° C. and treated portionwise with sodium borohydride. After stirring 1 hour at 5° C., water (150 ml) was added, the solvent was evaporated, the residue was extracted with dichloromethane and the organic extracts were dried (magnesium sulphate), filtered and evaporated. Treatment of the oil with ethereal hydrogen chloride gave the title compound, mp 126°-128° C. (methanol-ethylacetatediethyl ether).

$^1$H nmr δ(DMSO-d$_6$)

1.15 (3H, d); 3.30-3.60 (9H, complex); 4.5 (2H, d); 6.85 (2H, d); 7.20 (2H, d); 8.15 (1H, broad s, exchanges with D$_2$O); 9.1-9.7 (2H, broad s, exchanges with D$_2$O).

EXAMPLE X 2

N-methyl-N-[2-(4-methylaminocarbonylmethoxyphenyl)-1-methylethyl]-α-aminoacetophenone N-methyl-2-(4-methylaminocarbonylmethoxyphenyl)-1-methylethanamine hydrochloride (2.73 g) was suspended in tetrahydrofuran (10 ml) containing triethylamine (6 ml) and a solution of α-bromoacetophenone (1.99 g) in tetrahydrofuran (10 ml) was added dropwise. After stirring overnight this solution was treated with saturated sodium carbonate solution, extracted with dichloromethane, the organic phase was dried (magnesium sulphate), filtered and evaporated to give a red oil which was used without further purification.

DEMONSTRATION OF EFFECTIVENESS OF COMPOUNDS (a) Anti-hyperglycaemic activity

Female CFLP mice, weighing approximately 25 g, were fasted for 24 hours prior to the study. The compounds under study were administered orally as an aqueous solution to each of 6 mice. 30 minutes later a blood sample (10 μl) was obtained from the tail for the analysis of blood glucose. Immediately after taking this blood sample, glucose (lg/Kg body weight) was administered subcutaneously to each mouse. 6 mice were given water as a control. Blood samples were then obtained from each mouse at 30 minute intervals for 120 minutes.

Compounds that produced a significant (P<0.05) reduction of blood glucose, compared with control mice given water, at any time interval, were considered active. The area under the blood glucose curve over the 2 hour period after the administration of the glucose was calculated for each compound and compared with the value for control animals.

| Example No. | Dose (μmol/Kg) | % Reduction in area under Blood Glucose Curve |
| --- | --- | --- |
| 1 | 25 | 15 |
| 2 | 25 | 48 |
| 3 | 12.5 | 47 |
| 4 | 1 | 44 |
| 5 | 2.5 | 37 |
| 6 | 50 | 25 |
| 7 | 5 | 58 |
| 8 | 0.5 | 52 |
| 9 | 2.5 | 42 |
| 10 | 0.2 | 43 |
| 11 | 2.5 | 33 |
| 12 | 0.2 | 26 |
| 13 | 0.2 | 51 |
| 14 | 0.2 | 40 |
| 15 | 0.2 | 53 |
| 16 | 0.5 | 28 |
| 17 | 0.1 | 35 |
| 18 | 25 | 40 |

(b) Effect on Energy Expenditure

The effect of the compounds on the energy expenditure of mice was demonstrated by means of the following procedure:

Female CFLP mice, each weighing approximately 24 g were given food and water ad lib before and during the experiment. The compounds were dissolved in water by addition of one mole of hydrochloric acid per mole of compound and these solutions were administered orally to each of 12 mice. A further 12 mice were dosed orally with water. The mice were placed in boxes through which air was drawn and the oxygen content of the air leaving the boxes were measured. The energy expenditure of the mice was calculated for 3 hours after dosing from the volume of air leaving the boxes and its oxygen content, following the principles described by J. B. de V. Weir, *J. Physiol.* (London), 109, 1–9 (1949).

| Example No. | Dose mg/kg p.o. | Mean Energy Expenditure (0–3 h) |
| --- | --- | --- |
| 1 | 18.2 | 113 |
| 2 | 18.2 | 138 |
| 3 | 21.4 | 177 |
| 5 | 25.5 | 113 |
| 7 | 20.5 | 175 |
| 8 | 22.9 | 167 |
| 9 | 22.1 | 189 |
| 10 | 23.1 | 164 |
| 11 | 20.3 | 138 |
| 12 | 25.6 | 151 |
| 13 | 25.9 | 147 |
| 14 | 25.9 | 147 |
| 15 | 22.7 | 147 |
| 16 | 29.0 | 135 |
| 17 | 21.6 | 150 |
| 18 | 25.2 | 153 |

We claim:
1. N-[2-(4-carbomethoxymethoxyphenyl)-1-methylethyl]-N-methyl-2-hydroxy-2-(3-chlorophenyl)ethanamine and pharmaceutically acceptable salts thereof.

* * * * *

UNITED STATES PATENT AND TRADEMARK OFFICE
CERTIFICATE OF CORRECTION

PATENT NO. : 4,803,293

DATED : February 7, 1989

INVENTOR(S) : John Berge et al.

It is certified that error appears in the above-identified patent and that said Letters Patent is hereby corrected as shown below:

Title page:

Abstract, 20th line after formula I, after "or" insert -- an ester or -- .

Signed and Sealed this

Twenty-sixth Day of December, 1989

*Attest:*

JEFFREY M. SAMUELS

*Attesting Officer*     *Acting Commissioner of Patents and Trademarks*